United States Patent [19]

Stuart et al.

[11] 4,116,958
[45] Sep. 26, 1978

[54] ORGANIC SYNTHETIC METHODS BENZYLPYRIMIDINE DERIVATIVES

[75] Inventors: Alexander Stuart, Bromley; Thomas Paterson, Gravesend, both of England

[73] Assignee: Burroughs Wellcome Co., N.C.

[21] Appl. No.: 295,890

[22] Filed: Oct. 10, 1972

[30] Foreign Application Priority Data

Oct. 12, 1971 [GB] United Kingdom ............... 47492/71
Dec. 10, 1971 [GB] United Kingdom ............... 57512/71

[51] Int. Cl.$^2$ .......................................... C07D 237/48
[52] U.S. Cl. ................................... 544/325; 544/323
[58] Field of Search ............................... 260/256.4 N

[56] References Cited

U.S. PATENT DOCUMENTS 3,819,629  6/1974  Roth et al. ................. 260/256.4 N

FOREIGN PATENT DOCUMENTS 957,797     5/1964   United Kingdom ................. 260/256.4
1,142,654   2/1969   United Kingdom ................. 260/256.4

OTHER PUBLICATIONS

Brit. J. Pharmacol. 6: 185–188 (1951), Falco et al.
JACS 73: 3758–3762 (1951), Falco et al.
J. Med. Pharm. Chem. 5:1103–1107, 1112, 1118 (1962) Roth et al.

Primary Examiner—Natalie Trousof
Attorney, Agent, or Firm—Donald Brown

[57]  ABSTRACT

A method of preparation of 2,4-diamino-5-benzylpyrimidines involving the reaction of a 2,4-diamino-5-substituted methyl pyrimidine, for example 2,4-diamino-5-hydroxymethylpyrimidine, with an appropriately substituted phenol.

4 Claims, No Drawings

ORGANIC SYNTHETIC METHODS BENZYLPYRIMIDINE DERIVATIVES

This invention relates to a process for the preparation of 2,4-diamino-5-benzylpyrimidines, to novel intermediates in the process and to an improved method for preparing 2,4-diamino-5-formylpyrimidine.

The outstanding antimicrobial properties of 2,4-diamino-5-benzylpyrimidines are well known in the art (see, for example Falco, E. A. et al., M. Am. Chem. Soc, 1951, 73, 3758). Recently it has been discovered that certain derivatives of this class, having dialkyl and alkoxy substitutions in the phenyl ring, e.g. the 3,5-diethyl-4-methoxy-substituted derivative, have particularly good antimalarial and antibacterial properties (cf. copending British Patent Applications Nos. 50350/70 and 9638/71).

One of the great problems associated with the investigation of therapeutic potentials of new compounds in the 2,4-diamino-5-benzylpyrimidine series has been the great difficulty in obtaining appropriately substituted starting materials in the classical syntheses described in, for example, United Kingdom Patent Specifications Nos. 957,797 and 1,142,654.

There has long been a need for a synthetic route which is relatively quick and which could provide a variety of compounds relatively easily without the necessity of costly and time consuming development work for the adaptation of known processes, so that adequate amounts of these materials could be made available in good quality and in a relatively short time for biological testing, fields trials and later for marketing.

It has now been found that certain 2,4-diamino-5-substituted methylpyrimidines react well with even very heavily substituted phenols, although in some cases, the low solubility of such compounds may necessitate the use of specific media.

Furthermore, one of the starting pyrimidine derivatives, viz 2,4-diamino-5-hydroxymethylpyrimidine hitherto not readily available, can advantageously be prepared by an improved method, which enhances the industrial applicability of the whole synthetic route.

In one aspect of the present invention there is provided a method for preparing a 2,4-diamino-5-benzylpyrimidine of formula (I):

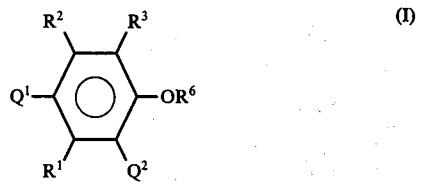

wherein one of $Q^1$ and $Q^2$ is a 2,4-diamino-pyrimidin-5-yl-methyl group, $R^1, R^2, R^3$ and the other Q group are each either a hydrogen or halogen atom or an alkyl or alkoxy group having from one to four, preferably from one to three, carbon atoms, provided that $Q^2$ is the said pyrimidinylmethyl group only when $Q^1$ is not a hydrogen atom, and $R^6$ is either a hydrogen atom or an alkyl group, which comprises reacting a compound of formula (V):

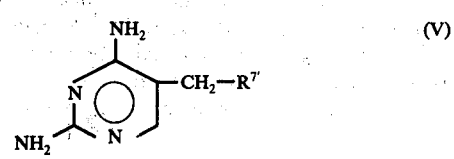

where $R^{7'}$ represent a hydroxyl group, halogen atom such as bromine or chlorine or represents the anionic residue of a carboxylic or sulphonic acid, with the appropriately substituted phenol of formula (II)

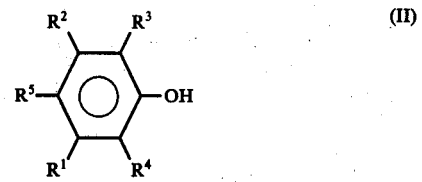

in a polar non-phenolic solvent capable of dissolving both reactants, wherein $R^1$, $R^2$ and $R^3$ are as hereinbefore defined and at least one of $R^4$ and $R^5$ is a hydrogen atom and the other is a hydrogen or halogen atom or an alkyl or alkoxy group as specified for Q, and, when $R^6$ is an alkyl group, alkylating the product with an alkylating agent $R^6Z$, wherein Z is a reactive atom or group.

$R^5$ and/or $R^1$ and $R^2$ can be hydrogen atoms, in which case the reaction provides compounds of special pharmacological interest. In particular, it is preferred that $R^3$ and $R^4$ are alkyl groups so that the final products of the reaction are 3,5-dialkyl-4-alkoxy-substituted benzyl derivatives, e.g. having a 3,5-diethyl substitution.

To obtain the highest yields and the best results, it is preferable that a strong acid catalyst be incorporated in the reaction medium. The acid catalyst may be a strong mineral acid, such as hydrochloric acid, either in water as a solvent or in a carboxylic acid, such as a lower fatty acid having up to four carbon atoms, for example acetic acid, or a sulphonic acid, for instance toluene-4-sulphonic acid as an alternative polar solvent. The amount of the acid catalyst may vary between broad limits but quantities from 0.2 to 4 N, conveniently about 0.3 N in aqueous or acetic acid medium, or 3 N in p-toluene sulphonic acid, are satisfactory for the purpose. The use of the specified organic solvents is particularly desirable with phenols carrying bulkier substituents, since these media provide higher concentrations for the reaction without precipitating the pyrimidine reactant.

For example, the reaction of 2,6-diethyl phenol with 5-hydroxymethylpyrimidine results in the preparation of 2,4-diamino-5-(3,5-diethyl-4-hydroxybenzyl)pyrimidine.

The steric influence of the groups in the ortho-positions relative to the hydroxy group of the compounds of formula (II) is an important factor in the above reaction. The larger these groups are, the more the hydroxy group tends to be forced out of the plane of the phenyl ring with consequential decrease of its activating influence on the ring. Therefore, as would be expected, yields utilising the process of the invention with a compound of formula (II) having t-butyl groups in the ortho-positions relative to the hydroxy group are substantially lower than with other less bulky substituents, because of the large steric effect of these groups.

Whenever the condensation reaction between the pyrimidine and phenol reactants takes place in a carboxylic or organic sulphonic acid medium, using a 2,4-diamino-5-hydroxy-methylpyrimidine as the starting material, a novel intermediate of formula (III) is formed

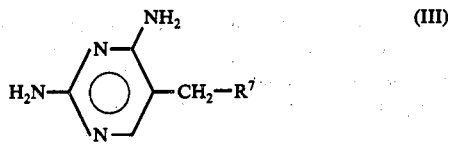
(III)

wherein $R^7$ is the anionic residue of the appropriate carboxylic acid or sulphonic acid. Compounds of formula (III), for instance the acetyl intermediate, have been detected and isolated and it has been found that they react with phenols of formula (II) to provide compounds of formula (I). Such compounds of formula (III) can also be prepared from 2,4-diamino-5-bromomethyl-pyrimidine by reaction with the appropriate sodium salt, e.g. sodium acetate.

In another aspect therefore the present invention provides compounds of formula (III).

If desired, the 2'- or 4'- hydroxy group of the compound of formula (I) can be converted to an alkoxy group by reacting the compound with an alkylating agent of formula $R^6Z$ where $R^6$ is an alkyl group and Z is a reactive atom, for example, a halogen atom, or, a reactive group, for example, a sulpate group.

Under practical conditions $R^6$ usually represents an alkyl or substituted alkyl group having up to 12, preferably from 1 to 8, most preferably from 1 to 4 carbon atoms.

The reaction of the hydroxyl group with $R^6Z$ can be accomplished in the presence of a base strong enough to form the phenate anion, for example, a base such as sodium hydroxide or potassium tertiary butoxide.

According to the present invention in another aspect, there is provided a compound of the general formula (I) whenever prepared by the hereinbefore defined process, and a novel compound of formula (IV)

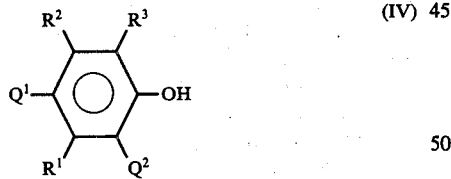
(IV)

wherein the substituents are as hereinbefore defined with regard to formula (I), provided that whenever $Q^1$ is a 2,4-diaminopyrimidin-5-yl-methyl group and whenever at least one of $R^3$ and $Q^2$ is an alkyl or alkoxy group, then at least one of $R^1$ and $R^2$ is a substituent other than a hydrogen atom. In addition to compounds of formula (IV), further intermediates according to formula (I) with $R^6$ as a hydrogen atom carrying only 3,5-dialkyl substitution on the 4-hydroxy-phenyl group, wherein each of the alkyl groups is selected from the class of methyl, ethyl, or propyl groups, e.g. 3,5-dimethyl, -diethyl, or -diisopropyl substituted compounds, are also provided according to the present invention.

The phenols according to formula (II) may be conveniently provided by well known general methods of chemistry such as by Friedel-Crafts condensations with phenols or the diazotisation and hydrolysis of the appropriate aniline derivatives.

Heretofore, the 2,4-diamino-5-hydroxymethylpyrimidine starting material of the invention has been prepared by a two-stage process which consisted firstly of a catalytic, hydrolytic hydrogenation of 2,4-diamino-5-cyanopyrimidine to form 2,4-diamino-5-formylpyrimidine, followed by reduction with sodium borohydride to form the 5-hydroxymethyl pyrimidine (see *Journal to Medicinal Chemistry*, 1968, 11, 1238). However, this process gave rather disappointing yields.

It has now been discovered that the hydrolytic hydrogenation of 2,4-diamino-5-cyanopyrimidine to 2,4-diamino-5-formylpyrimidine can advantageously be carried out with Raney nickel or with nickel-aluminum alloy as a catalyst in the presence of an acid. In this connection, it should be noted that formic acid is the acid of choice in view of the very high yields obtained. However, ethanolic hydrochloric acid can also be used. A considerable improvement in the yield is obtained and the product is eminently suitable for further processing to provide 2,4-diamino-5-hydroxymethyl-pyrimidine on further selective reduction, for instance with borohydride, as disclosed in the literature.

Application of the process described herein to the compounds of formula (I), wherein $Q_1$ is the 2,4-diamino-pyrimidin-5-yl-methyl group, $R^1$ and $R^2$ are hydrogen atoms, and $R^3$ and $Q^2$ are alkyl groups having from 2 to 4 carbon atoms, is also described in the provisional specification of co-pending British Patent Application 47491/71.

It is to be noted that the compounds: 2,4-diamino-5-(3,5-dimethyl-4-methoxybenzyl)pyrimidine; 2,4-diamino-5-(2,3,5,6-tetramethyl-4-methoxybenzyl)-pyrimidine; 2,4-diamino-5-(2,3,4-trimethoxybenzyl)-pyrimidine; 2,4-diamino-5-(2-methoxy-3,5-dimethylbenzyl)pyrimidine and 2,4-diamino-5-(2,3,5,6-tetramethyl-4-ethoxybenzyl)pyrimidine are novel and have antibacterial and/or antimalarial activity.

Compounds of formula (V) where $R^{7'}$ represents a bromine atom can be prepared by bromination of the corresponding hydroxy compound of formula (V).

The invention will now be further described, by way of illustration only, with reference to the following Examples.

EXAMPLE 1

2,4-Diamino-5-cyanopyrimidine (1 g) prepared as described by Huber, W., *Journal of the American Chemical Society*, 1943, 65, 2223 was dissolved in 75% formic acid (15 ml.) and 50:50 Ni-Al alloy (1 g.) was added. The suspension was refluxed for 1 hour, filtered while hot, and then evaporated to dryness on a rotary-evaporator. The residue was diluted with water and made alkaline with sodium hydroxide solution. The precipitate was removed by filtration and purified by recrystallisation from water (100 ml.) or by dissolving in 50% acetic acid and neutralising with base (i.e. sodium hydroxide or ammonium hydroxide solutions). M.p 273°–275° C. (decomp.) colourless needles from water. Yield 66% of the theoretical.

Elemental analysis, u.v. spectra, i.r. spectra, n.m.r. spectra, and mass spectra, t.l.c. data, v.p.c. data all showed the product to be 2,4-diamino-5-formylpyrimidine.

2,4-Diamino-5-hydroxymethylpyrimidine

This was prepared from the 2,4-diamino-5-formylpyrimidine prepared above by reduction using the conditions described in the *Journal of Medicinal Chemistry*, 1968. 11, 1238.

2,4-Diamino-5-(3,5-diethyl-4-hydroxybenzyl)pyrimidine 2,4-Diamino-5-hydroxymethyl pyrimidine (1.4 g. 0.01 mole) and 2,6-diethylphenol (1.6 g., 0.01 mole) in glacial acetic acid (100 ml) containing conc. hydrochloric acid (3 ml.), were heated on a steam-bath. The initial precipitate slowly dissolved After 5 hours the reaction was cooled and evaporated to dryness on a rotary-evaporator. The residue was treated with acetone (50 ml.) and triturated to give a granular solid.

The solid was filtered and recrystallised from water to give the product as the hydrochloride, m.p. 277°-279° C.

Alternatively, the crude solid or the hydrochloride was dissolved in hot water and neutralised with a solution of sodium hydrogen carbonate to give the free base. Recrystallisation from aqueous ethanol gave colourless needles of 2,4-diamino-5-(3,5-diethyl-4-hydroxybenzyl)-pyrimidine, m.p. 204°-205° C. Yield 66% on theory.

EXAMPLE 2

2,4-Diamino-5-hydroxymethylpyrimidine (1.4 g.), prepared as in Example 1, and 2,6-diethylphenol (1.6 g.) in toluene-4-sulphonic acid (10 g.) containing conc. hydrochloric acid (3 ml.) were heated on the steam-bath for 6 hours. The solution was cooled, diluted with ether and the ether decanted. The residue was treated with a soln. of sodium hydrogen carbonate and the solid filtered off. Recrystallisation from aqueous ethanol gave colourless needles of 2,4-diamino-5-(3,5-diethyl-4-hydroxybenzyl)pyrimidine, m.p. 200°-202° C.

EXAMPLE 3

The procedure of Example 1 was repeated with 2,6-diisopropyl phenol as a reactant. 2,4-Diamino-5-(3,5-diisopropylhydroxy-benzyl) pyrimidine was produced in a 40% yield (m.p. of the free base is 244° to 246° C.).

EXAMPLE 4

The 4-hydroxybenzylpyrimidines prepared according to the processes defined in the previous Examples were converted into the corresponding 4-methoxy derivatives utilising the following procedure.

The appropriate 5-(4-hydroxybenzyl)pyrimidine, 0.005 mole) was dissolved in dry dimethylsulphoxide (10 ml.), and sodium alkoxide (slightly in excess of 0.005 mole) was added. Methyl iodide., (slightly in excess of 0.005 mole) was added and the stoppered reaction flask left in the dark for 3–4 days.

The solution was then poured into water and the product removed by filtration or extraction into ethyl acetate and evaporation. Recrystallisation was effected from aqueous ethanol.

It was found that satisfactory methylation occurred for both the hydroxybenzylpyrimidines, providing 2,4-diamino-5-(3,5-diethyl-4-methoxy)pyrimidine and 2,4-diamino-5-(3,5-diisopropyl-4-methoxy)pyrimidine.

EXAMPLE 5

2,4-Diamino-5-hydroxymethylpyrimidine (1.4 g.) prepared as in Example 1 and 2,6-dimethylphenol (1.1 g.) were refluxed in water (30 ml.), containing conc. hydrochloric acid (1 ml.) and a little acetone to facilitate the dissolution of the phenol. After 5 hours reflux, the reaction was cooled and the product filtered. Recrystallisation from water gave the product as the hydrochloride m.p. 280° (slow decomposition). The free base was obtained by the usual means, m.p. 242°-244° C.

EXAMPLE 6

The procedure according to Example 2 was repeated with 2,6-dimethylphenol, 2,3,5,6-tetramethylphenol, and 2,6-dimethoxyphenol to obtain the appropriately substituted 2,4-diamino-5-benzylpyrimidines i.e. 2,4-diamino-5(3,5-dimethyl-4-hydroxybenzyl)pyrimidine, 2,4-diamino-5-(2,3,5,6-tetramethyl-4-hydroxybenzyl)-pyrimidine and a mixture 2,4-diamino-5-(3,5-dimethoxy-4-hydroxybenzyl)pyrimidine and 2,4-diamino-5-(2,4-dimethoxy-3-hydroxybenzyl)pyrimidine.

EXAMPLE 8

The procedure of Example 1 was repeated, but the 2,6-diethylphenol was replaced with 2,6-dimethylphenol.

2,4-Diamino-5-(3,5-dimethyl-4-hydroxybenzyl)-pyrimidine was produced in a yield of 58%. The melting point of the hydrochloride is 280° C. (slow decomp.)

EXAMPLE 9

The procedure of Example 1 was repeated utilising phenol in place of the 2,6-diethylphenol. 2,4-Diamino-5-(4-hydroxybenzyl)pyrimidine was isolated in a satisfactory yield.

EXAMPLE 10

The procedure of Example 1 was repeated utilising 2,4-dimethylphenol in place of the 2,6-diethylphenol. 2,4-Diamino-5-(2-hydroxy-3,5-dimethylbenzyl)pyrimidine was obtained in a satisfactory yield. The melting point of the hydrochloride was found to be 279°-281° C. (dec.)

EXAMPLE 11

The procedure of Example 1 was repeated utilising 2,3,5,6-tetramethylphenol in place of the 2,6-diethylphenol. 2,4-Diamino-5-(2,3,5,6-tetramethyl-4-hydroxybenzyl)pyrimidine was obtained in a yield of 60% (melting point of hydrochloride greater than 330° C.)

EXAMPLE 12

The procedure of Example 1 was repeated using 2,6-dimethoxyphenol in place of the 2,6-diethylphenol. A good yield of a mixture of 2,4-diamino-5-(3,5-dimethoxy-4-hydroxybenzyl)pyrimidine and 2,4-diamino-5-(2,4-dimethoxy-3-hydroxybenzyl)pyrimidine was obtained. These components of the mixture could be separated by fractional crystallisation. The latter melting at between 246° and 248° C. (free base).

EXAMPLE 13

The procedure of Example 1 was repeated utilising 2-methoxyphenol in place of the 2,6-diethylphenol. The 2,4-diamino-5-(3-methoxy-4-hydroxybenzyl)pyrimidine product was isolated in the form of the hydrochloride salt. The melting point was 263°-265° C.

EXAMPLE 14

The methylation procedure described in Example 4 was repeated with the products specified in Examples 12 and 13, to obtain the corresponding 2,4-diamino-5-benzylpyrimidines having the following substitutions on the benzyl ring:
2,3,4-trimethoxy,
3,4,5-trimethoxy,
3,4-dimethoxy.

EXAMPLE 15

The methylation procedure described in Example 4 was repeated with the products specified in Examples 5,6,9,10,12 and 13 to obtain the corresponding 2,4-diamino-5-benzylpyrimidines having the following substitutions on the benzyl ring:
3',5'-dimethyl-4-methoxy,
2,3,5,6-tetramethyl-4-methoxy,
2,3,4-trimethoxy,
4-methoxy,
3,5-dimethyl-2-methoxy, and
3,4-dimethoxy.

EXAMPLE 16

Compounds obtained in Examples 1 to 3, and 5 to 13 were ethylated with ethyl iodide substantially as described in Example 4 to obtain, for instance, 2,4-diamino-5-(2,3,5,6-tetramethyl-4-ethoxybenzyl)pyrimidine.

EXAMPLE 17

To 2,4-diamino-5-bromomethylprimidine hydrobromide (3 g.) in acetic acid (50 ml.) was added anhydrous sodium acetate (3.2 g.). The mixture was heated for 15 minutes on a steam bath, filtered and cooled.

The while solid was filtered off and recrystallised from acetic acid. Yield 2.3 g. M.pt 292°–295° C. (decomp.).

T.l.c. showed the product to be a single spot and of the same Rf as the intermediate formed in situ from 2,4-diamino-5-hydroxymethylpyrimidine. This compound was shown to be 2,4-diamino-5-(acetoxymethyl)-pyrimidine. Using the experimental conditions described in Example 1 the acetoxymethyl derivative was converted to 2,4-diamino-5-(3,5-diethyl-4-hydroxybenzy)pyrimidine (m.p. 204°–205° C.)

EXAMPLE 18

2,4-Diamino-5-hydroxymethylpyrimidine (1.4 g.) was dissolved in 4-toluene sulphonic acid (10 g.) at 120° C. and concentrated hydrochloric acid (3 ml.) was added. The initial precipitate was redissolved on stirring at 120° C. The reaction mixture was stirred for two hours and then poured into 50 ml. of acetone. Colourless plates of 2,4-diamino-5-(4-toluenesulphonyloxymethyl) pyrimidine were filtered off. (m.p. 176°–178° C.).

This compound was then reacted with 2,6-diethylphenol as described in Example 1 to yield 2,4-diamino-5-(3,5-diethyl-4-hydroxybenzyl)pyrimidine (m.p. 204°–205° C.).

EXAMPLE 19

2,4-diamino-5-bromomethylpyrimidine was reacted with 2,6-diethylphenol using the experimental conditions described in Example 1. 2,4-diamino-5-(3,5-diethyl-4-hydroxybenzyl)pyrimidine was obtained in a yield of approximately 65%.

We claim:

1. A 2,4-diamino-5-benzylpyrimidine compound of the formula

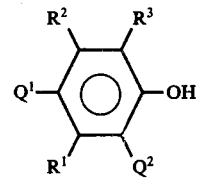

wherein $Q^1$ is a 2,4-diaminopyrimidin-5-yl-methyl group and $R^1$, $R^2$, $R^3$ and $Q^2$ are alkyl groups of 1 to 4 carbon atoms.

2. A 2,4-diamino-5-benzylpyrimidine compound of the formula

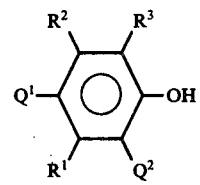

wherein $Q^2$ represents a 2,4-diaminopyrimidin-5-yl-methyl group, $R^1$ and $R^2$ represent hydrogen atoms and $Q^1$ and $R^3$ represent alkyl groups of 1 to 4 carbon atoms.

3. The compound 2,4-diamino-5-(2,3,5,6-tetramethyl-4-hydroxybenzyl)pyrimidine.

4. The compound 2,4-diamino-5-(2-hydroxy-3,5-dimethylbenzyl)pyrimidine.

* * * * *